US008260576B2

(12) United States Patent  
Iwazaki et al.

(10) Patent No.: US 8,260,576 B2
(45) Date of Patent: Sep. 4, 2012

(54) EXHAUST GAS SENSOR ABNORMALITY DIAGNOSTIC DEVICE (75) Inventors: Yasushi Iwazaki, Ebina (JP); Hiroshi Sawada, Gotemba (JP); Takahiro Joko, Sunto-gun (JP); Masaya Kawaji, Toyota (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/287,460

(22) Filed: Nov. 2, 2011

(65) Prior Publication Data

US 2012/0046910 A1 Feb. 23, 2012

Related U.S. Application Data (62) Division of application No. 12/226,774, filed as application No. PCT/JP2007/062785 on Jun. 26, 2007.

(30) Foreign Application Priority Data

Jul. 3, 2006 (JP) ................................. 2006-183597

(51) Int. Cl.
G06F 11/30 (2006.01)

(52) U.S. Cl. ...................................................... 702/183

(58) Field of Classification Search .................... 702/183
See application file for complete search history.

(56) References Cited

U.S. PATENT DOCUMENTS

| 6,105,552 A | 8/2000 | Arisawa et al. |
| 6,711,932 B2 * | 3/2004 | Iwazaki et al. ................. 73/1.06 |
| 7,340,945 B2 | 3/2008 | Tashiro |
| 2004/0261498 A1 | 12/2004 | Hattori |

FOREIGN PATENT DOCUMENTS

| JP | A-08-327586 | 12/1996 |
| JP | A-2003-014683 | 1/2003 |
| JP | A-2004-170309 | 6/2004 |
| JP | A-2004-353494 | 12/2004 |
| JP | A-2005-042676 | 2/2005 |

OTHER PUBLICATIONS

Office Action issued on Nov. 25, 2011 in related U.S. Appl. No. 12/226,774.
Related U.S. Appl. No. 12/226,774 filed Oct. 28, 2008 to Yasushi Iwazaki et al.

* cited by examiner

Primary Examiner — Aditya Bhat
(74) Attorney, Agent, or Firm — Oliff & Berridge, PLC (57) ABSTRACT

An exhaust gas sensor abnormality diagnostic device includes an exhaust gas sensor, and a judgment means that judges whether execution conditions are established for making an abnormality diagnosis of element breakage in the exhaust gas sensor. The device also includes an abnormality diagnosis means that makes the abnormality diagnosis in accordance with an output signal generated by the exhaust gas sensor. Further, when the integrated value of intake air amounts of an internal combustion engine is not smaller than a predetermined value, the judgment means judges that the execution conditions are established. The abnormality diagnosis means cancels the establishment of the execution conditions when an intake air amount of the internal combustion engine remains less than a predetermined value for a predetermined period of time.

2 Claims, 4 Drawing Sheets

Normal Status

*Fig. 3A*

Abnormal Status

*Fig. 3B*

Fuel cut Status

EXHAUST GAS SENSOR ABNORMALITY DIAGNOSTIC DEVICE

The present application is a divisional application of application Ser. No. 12/226,774 filed Oct. 28, 2008, which is a National Stage Application of PCT/JP2007/062785 filed Jun. 26, 2007, which claims priority from Japanese Patent Application No. 2006-183597 filed Jul. 3, 2006. The disclosure of each of the prior applications is hereby incorporated by reference in its entirety.

TECHNICAL FIELD

The present invention relates to an abnormality diagnostic device for an exhaust gas sensor, and more particularly to an abnormality diagnostic device suitable for detecting a broken sensor element of an exhaust gas sensor.

BACKGROUND ART

A known device disclosed, for instance, in JP-A-2003-14683 detects an abnormality caused by a broken element of an oxygen sensor (hereinafter also referred to as a "sensor") installed in the exhaust path of an internal combustion engine. The oxygen sensor includes a sensor element, which is positioned between the atmosphere and exhaust gas, and outputs a voltage according to the oxygen partial pressure difference between the exhaust gas and the air in the atmospheric layer. When the resulting voltage output pattern indicates that the oxygen partial pressure difference is small or reversed, the device concludes that the sensor element is defective and then makes an abnormality diagnosis.

Patent Document 1:
Japanese Patent Laid-Open No. 2003-14683
Patent Document 2:
Japanese Patent Laid-Open No. 2004-353494
Patent Document 3:
Japanese Patent No. 3562030

DISCLOSURE OF INVENTION

Problem to be Solved by the Invention

However, even when the sensor element of the oxygen sensor becomes defective, that abnormal sensor may exhibit, depending on the operating status of the internal combustion engine, the same output pattern as when the sensor is normal. Conversely, a normal oxygen sensor may exhibit an output pattern similar to the one exhibited when the element is broken. More specifically, while the exhaust gas is lean, the oxygen partial pressure does not decrease even if the exhaust gas enters the atmospheric layer through a defective portion due to sensor element breakage. In this instance, the resulting output pattern may be similar to the one exhibited when the sensor is normal. It is also conceivable that even if the sensor element is broken, the oxygen partial pressure may not decrease, depending on the intake air amount for the internal combustion engine, due to the failure of the exhaust gas to enter the atmospheric layer from the defective portion. Therefore, the device may erroneously judge the oxygen sensor to be normal when its element is broken. As a result, the device described above is not a reliable abnormality diagnostic device for the sensor.

The present invention has been made to solve the above problem. It is an object of the present invention to provide an abnormality diagnostic device that is capable of accurately diagnosing an abnormality caused by a broken element of an exhaust gas sensor.

Means for Solving the Problem

First aspect of the present invention is an exhaust gas sensor abnormality diagnostic device comprising:
an exhaust gas sensor which is positioned in an exhaust path of an internal combustion engine, includes a sensor element positioned between external air and exhaust gas, and generates an output signal correlated with the oxygen partial pressure difference between the external air and the exhaust gas;
judgment means which judges whether execution conditions are established for making an abnormality diagnosis of element breakage in the exhaust gas sensor; and
abnormality diagnosis means which, when the execution conditions are established, makes the abnormality diagnosis in accordance with an output signal generated by the exhaust gas sensor;
wherein, during a lean period during which an air-fuel ratio of the exhaust gas is lean, the judgment means concludes that the execution conditions are not established.

Second aspect of the present invention is the exhaust gas sensor abnormality diagnostic device according to the first aspect, wherein the lean period contains a period during which a fuel cut is performed in the internal combustion engine.

Third aspect of the present invention is the exhaust gas sensor abnormality diagnostic device according to the first or the second aspects, wherein the abnormality diagnosis means makes the abnormality diagnosis in accordance with an output signal that is generated by the exhaust gas sensor during a period during which the air-fuel ratio of the exhaust gas is lean.

Fourth aspect of the present invention is an exhaust gas sensor abnormality diagnostic device comprising:
an exhaust gas sensor which is positioned in an exhaust path of an internal combustion engine, includes a sensor element positioned between external air and exhaust gas, and generates an output signal correlated with the oxygen partial pressure difference between the external air and the exhaust gas;
judgment means which judges whether execution conditions are established for making an abnormality diagnosis of element breakage in the exhaust gas sensor; and
abnormality diagnosis means which, when the execution conditions are established, makes the abnormality diagnosis in accordance with an output signal generated by the exhaust gas sensor;
wherein the judgment means includes integrated intake air amount acquisition means for acquiring an integrated value of intake air amounts of the internal combustion engine and judges that the execution conditions are established when the integrated value is not smaller than a predetermined value.

Fifth aspect of the present invention is the exhaust gas sensor abnormality diagnostic device according to the fourth aspect, wherein the integrated intake air amount acquisition means resets the integrated value when an air-fuel ratio of the exhaust gas is lean.

Sixth aspect of the present invention is the exhaust gas sensor abnormality diagnostic device according to the fourth or the fifth aspects, wherein the integrated intake air amount acquisition means resets the integrated value when an intake air amount is not greater than a predetermined value.

Seventh aspect of the present invention is an exhaust gas sensor abnormality diagnostic device comprising:

an exhaust gas sensor which is positioned in an exhaust path of an internal combustion engine, includes a sensor element positioned between external air and exhaust gas, and generates an output signal correlated with the oxygen partial pressure difference between the external air and the exhaust gas;

judgment means which judges whether execution conditions are established for making an abnormality diagnosis of element breakage in the exhaust gas sensor; and abnormality diagnosis means which, when the execution conditions are established, makes the abnormality diagnosis in accordance with an output signal generated by the exhaust gas sensor;

wherein the abnormality diagnosis means includes cancellation means which cancels the establishment of the execution conditions when an intake air amount of the internal combustion engine remains not greater than a predetermined value for a predetermined period of time.

Advantages of the Invention

During a lean period during which the air-fuel ratio of exhaust gas is lean, the first aspect of the present invention prohibits the abnormality diagnosis of the exhaust gas sensor. A fuel-lean exhaust gas has a high oxygen partial pressure. Therefore, even when such exhaust gas flows toward external air side through a break in the sensor element, a sensor output signal for detecting an abnormality caused by element breakage cannot be detected. Therefore, the present invention prohibits the abnormality diagnosis during the above-mentioned period to avoid erroneously judging the sensor to be normal when it is abnormal due to its broken element. This makes it possible to enhance the accuracy of detecting an abnormality caused by a broken element.

While a fuel cut is performed in an internal combustion engine, the second aspect of the present invention can prohibit the abnormality diagnosis of the exhaust gas sensor. While a fuel cut is performed, the atmosphere flows in an exhaust path. Therefore, the present invention prohibits the abnormality diagnosis during the above-mentioned period to avoid erroneously judging the sensor to be normal when it is abnormal due to its broken element. This makes it possible to enhance the accuracy of detecting an abnormality caused by a broken element.

When the integrated value of the intake air amounts Ga is not smaller than a predetermined value, the fourth aspect of the present invention makes an abnormality diagnosis of the exhaust gas sensor. The amount of exhaust gas flowing in the exhaust path increases with an increase in the integrated value of the intake air amounts Ga. Therefore, when the integrated value of the intake air amounts Ga is large, a large amount of exhaust gas may flow from a break in the element in the exhaust path toward the external air. Therefore, the present invention makes an abnormality diagnosis of the exhaust gas sensor in the above situation to avoid erroneously judging the sensor to be normal when it is abnormal due to its broken element. This makes it possible to enhance the accuracy of detecting an abnormality caused by a broken element.

If the intake air amount Ga remains extremely small for a predetermined period of time, the seventh aspect of the present invention nullifies the conditions for making an abnormality diagnosis of the exhaust gas sensor. While the intake air amount Ga is small, the exhaust gas flowing from a break in the element in the exhaust path toward the external air may flow back toward the exhaust path. If this situation continues, a sensor output signal indicating whether the sensor is abnormal will not be detected eventually. Therefore, if the intake air amount Ga remains small for a predetermined period of time, the present invention cancels the execution of an abnormality diagnosis and judges again whether the execution conditions are established. This makes it possible to avoid erroneously judging the sensor to be normal when it is abnormal due to its broken element, thereby enhancing the accuracy of detecting an abnormality caused by a broken element.

DESCRIPTION OF REFERENCE CHARACTERS 10 internal combustion engine
12 intake path
14 exhaust path
16 air flow meter
18 throttle valve
20 throttle sensor
22 injector
24 crankshaft
26 crank angle sensor
28 catalyst
30 air-fuel ratio sensor (A/F sensor)
40 oxygen sensor
42 cover
44 sensor element
46 diffusion resistance layer
48 exhaust side electrode
50 solid electrolyte layer
52 atmosphere side electrode
54 atmospheric chamber
56 heater
60 break

BEST MODE FOR CARRYING OUT THE INVENTION

An embodiment of the present invention will now be described with reference to the accompanying drawings. Like elements in the drawings are assigned the same reference numerals and will not be redundantly discussed. It should be understood that the present invention is not limited to the embodiment described below.

First Embodiment

Configuration of First Embodiment

Figure 1:
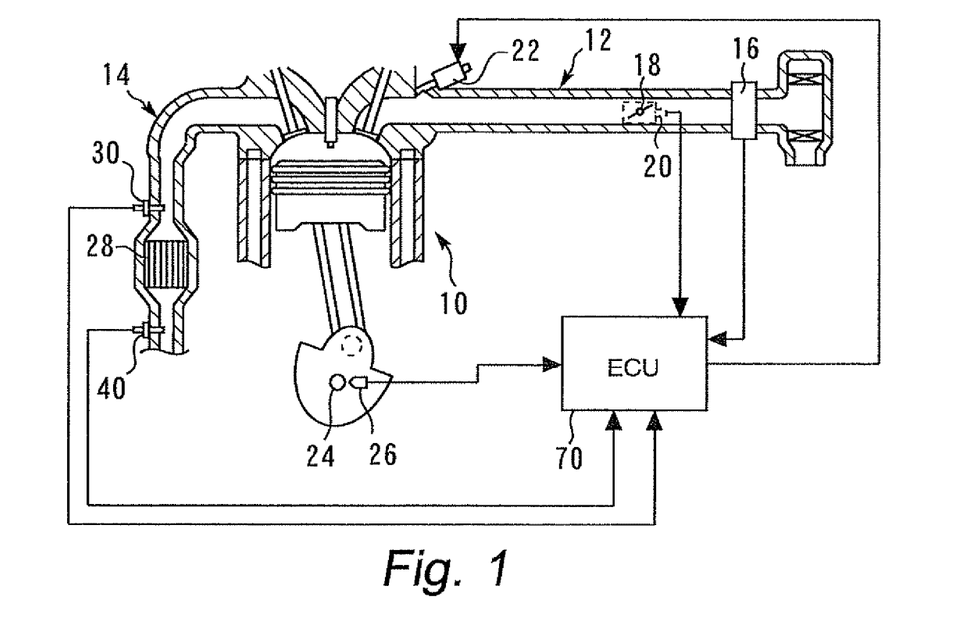
FIG. 1 is a schematic diagram showing the configuration related to the first embodiment of the present invention.

FIG. 1 is a diagram illustrating the hardware configuration of a first embodiment of the present invention. As shown in FIG. 1, the system according to the first embodiment includes an internal combustion engine 10. The internal combustion engine 10 communicates with an intake path 12 and an exhaust path 14. An air flow meter 16 is installed in the intake path 12 to detect an intake air amount. A throttle valve 18 is installed downstream of the air flow meter 16. A throttle sensor 20 is installed near the throttle valve 18 to detect a throttle opening angle.

An injector 22 is positioned in each cylinder of the internal combustion engine 10 to inject fuel into an intake port. A crank angle sensor 26 is installed near a crankshaft 24 of the internal combustion engine to detect the rotation angle of the crankshaft 24. The output of the crank angle sensor can be used to detect, for instance, an engine speed NE and the rotational position of the crankshaft 24.

An exhaust purification catalyst (hereinafter may be abbreviated to "catalyst") 28 is installed in the exhaust path 14 of the internal combustion engine 10. The catalyst 28, which is a three-way catalyst, simultaneously removes CO, HC (hydrocarbon), and $NO_x$, which are harmful components of exhaust gas, at an air-fuel ratio close to the stoichiometric air-fuel ratio.

An air-fuel ratio sensor (A/F sensor) 30 is installed in the exhaust path 14 and positioned upstream of the catalyst 28. The air-fuel ratio sensor 30 linearly detects the oxygen concentration in the exhaust gas. This sensor detects the air-fuel ratio of an air-fuel mixture burned in the internal combustion engine 10, in accordance with the oxygen concentration in the exhaust gas flowing into the catalyst 28.

Further, an oxygen sensor 40 is installed in the exhaust path 14 and positioned downstream of the catalyst 28. The oxygen sensor 40 detects whether the oxygen concentration in the exhaust gas is higher or lower than a predetermined value. This sensor outputs a voltage higher than a predetermined voltage (e.g., 0.45 V) when the exhaust air-fuel ratio at the sensor position is fuel-richer than the stoichiometric air-fuel ratio and outputs a voltage lower than the predetermined voltage when the exhaust air-fuel ratio is leaner than the stoichiometric air-fuel ratio. Therefore, the oxygen sensor 40 can judge whether a fuel-rich exhaust gas (containing HC and CO) or a fuel-lean exhaust gas (containing $NO_x$) is flowing downstream of the catalyst 28.

The device according to the present embodiment includes an ECU (Electronic Control Unit) 70. The ECU 70 is connected, for instance, to the aforementioned various sensors and injector 22. The ECU 70 is capable of controlling the operating status of the internal combustion engine 10 in accordance with outputs from the sensors.

[Configuration of Oxygen Sensor]

Figure 2:
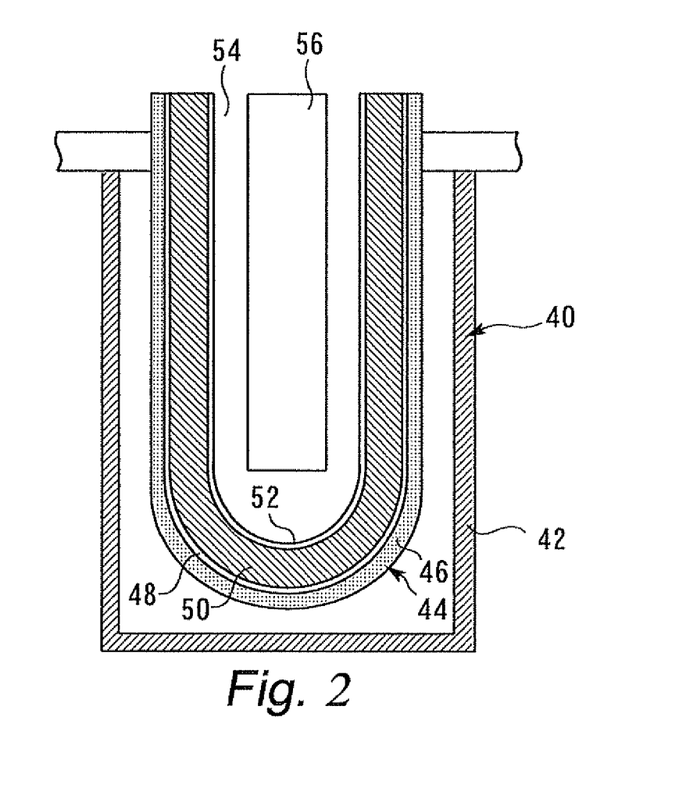
FIG. 2 is a diagram illustrating the configuration of the oxygen sensor used in the first embodiment of the present invention.

FIG. 2 is a diagram illustrating the configuration of the oxygen sensor 40 used in the first embodiment of the present invention. As described earlier, the oxygen sensor 40 shown in FIG. 2 is installed in the exhaust path 14 of the internal combustion engine 10 and used to detect the air-fuel ratio of the exhaust gas flowing downstream of the catalyst 28. The oxygen sensor 40 has a cover 42, which is installed in the exhaust path 14 so as to be exposed to the exhaust gas.

There is a hole (not shown) in the cover 42 to introduce the exhaust gas inside the cover 42. A sensor element 44 is positioned inside the cover 42. The sensor element 44 has a tubular structure, one end (the lower end as viewed in FIG. 2) of which is closed. The outer surface of the tubular structure is covered with a diffusion resistance layer 46. The diffusion resistance layer 46 is made of a heat-resistant, porous substance such as alumina. This layer 46 controls the diffusion speed of the exhaust gas near the surface of the sensor element 44.

Inside the diffusion resistance layer 46 are an exhaust side electrode 48, a solid electrolyte layer 50, and an atmosphere side electrode 52. The exhaust side electrode 48 and atmosphere side electrode 52 are composed of Pt or other highly catalytic, noble metal. These electrodes are electrically connected to a control circuit, which will be described later. The solid electrolyte layer 50 is a sintered body that contains, for instance, $ZrO_2$. It permits the conduction of oxygen ions.

An atmospheric chamber 54, which is exposed to the atmosphere, is formed inside the sensor element 44. A heater 56 for heating the sensor element 44 is mounted in the atmospheric chamber 54. The sensor element 44 exhibits a stable output characteristic at an activation temperature of approximately 400° C. The heater 56 is electrically connected to a control circuit and capable of heating the sensor element 44 and maintaining it at an appropriate temperature.

[Principles of Oxygen Sensor Abnormality Detection]

Figure 3A:
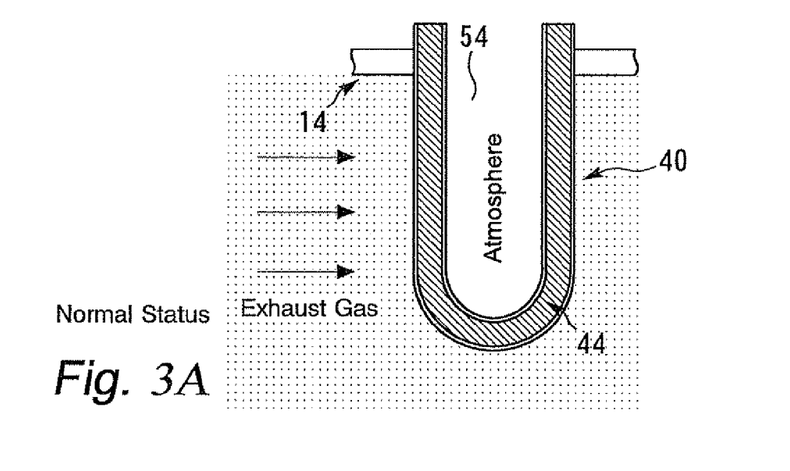
FIG. 3A is a diagram showing the principles of detecting the abnormality of the oxygen sensor.

The principles of detecting the abnormality of the oxygen sensor 40 will now be described with reference to FIGS. 3A to 3C. FIG. 3A illustrates the ambient environment of the oxygen sensor 40, which is installed in the exhaust path 14 of the internal combustion engine 10. As described earlier, the oxygen sensor 40 generates an output according to the oxygen concentration difference between the atmospheric layer 54 side and exhaust path 14 side of the sensor element 44. If the oxygen sensor 40 is normal, that is, the sensor element 44 is not defective, as indicated in FIG. 3A, the exhaust gas flowing in the exhaust path 14 does not mix into the atmospheric layer 54. Therefore, the oxygen concentration on the exhaust path 14 side is constantly lower than that on the atmospheric layer 54 side. Thus, while the oxygen sensor 40 is normal, it constantly generates a positive voltage value.

However, when the oxygen sensor 40 becomes defective due, for instance, to its broken element, the exhaust gas in the exhaust path 14 may flow into the atmospheric layer 54. FIG. 3B shows a state where the sensor element 44 is broken. When the sensor element 44 is broken, exhaust pressure may force the exhaust gas in the exhaust path 14 into the atmospheric layer 54 from a break 60 in the element, as shown in FIG. 3B. In this instance, the oxygen sensor 40 does not generate any output because there is no oxygen concentration difference between the atmospheric layer 54 side and exhaust path 14 side of the sensor element 44.

Figure 3B:
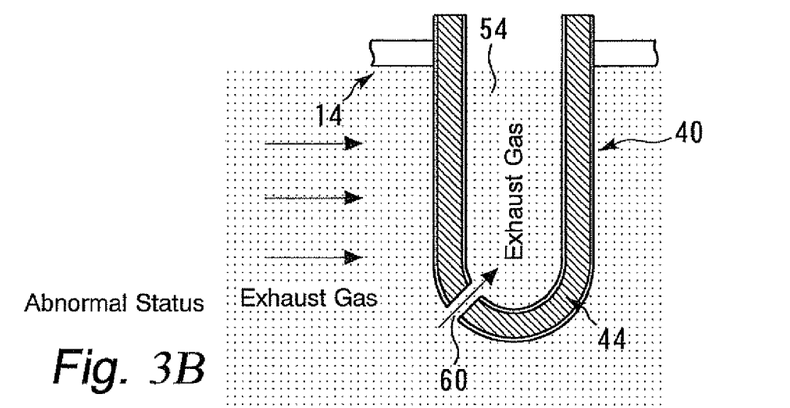
FIG. 3B is a diagram showing the principles of detecting the abnormality of the oxygen sensor.
Figure 3C:
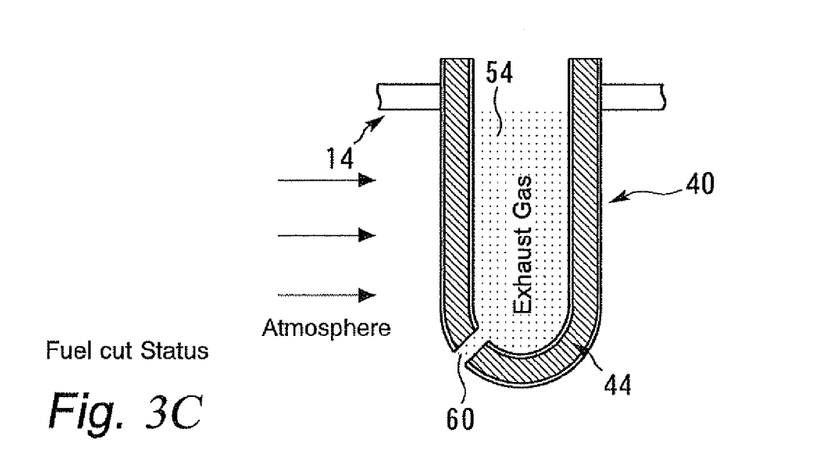
FIG. 3C is a diagram showing the principles of detecting the abnormality of the oxygen sensor.

FIG. 3C illustrates the ambient environment of the oxygen sensor 40 that prevails when a fuel cut is performed in the internal combustion engine 10 subsequent to the state shown in FIG. 3B. In the internal combustion engine 10, a fuel cut is frequently performed, depending, for instance, on the operating status, to temporarily halt a fuel injection operation. When a fuel cut is performed, the atmosphere flows into the exhaust path 14. Therefore, as indicated in FIG. 3C, when a fuel cut is performed after the exhaust gas enters the atmospheric layer 54 from the break 60 in the element of the oxygen sensor 40, the oxygen concentration difference between the atmospheric layer 54 side and exhaust path 14 side of the sensor element 44 is reversed, thereby causing the sensor to generate a negative voltage. Consequently, a break in the sensor element can be accurately detected by detecting the negative voltage from the sensor output.

[Characteristic Operation of Present Embodiment]

A characteristic operation of the present embodiment will now be described with reference to FIG. 4 or 5. As described earlier, when the oxygen sensor 40 outputs a negative value, it can be definitely concluded that the oxygen sensor 40 is abnormal with its element broken. However, even when the oxygen sensor 40 is abnormal with its element broken, the sensor may fail to output a negative value, depending on the operating status of the internal combustion engine, and exhibit the same output pattern as that exhibited when the sensor is normal. As such being the case, the present embodiment performs an abnormality diagnosis of the oxygen sensor 40 that further incorporates the following conditions with a view toward enhancing the accuracy of detecting an abnormality caused by a broken element of the oxygen sensor 40.

Figure 4:
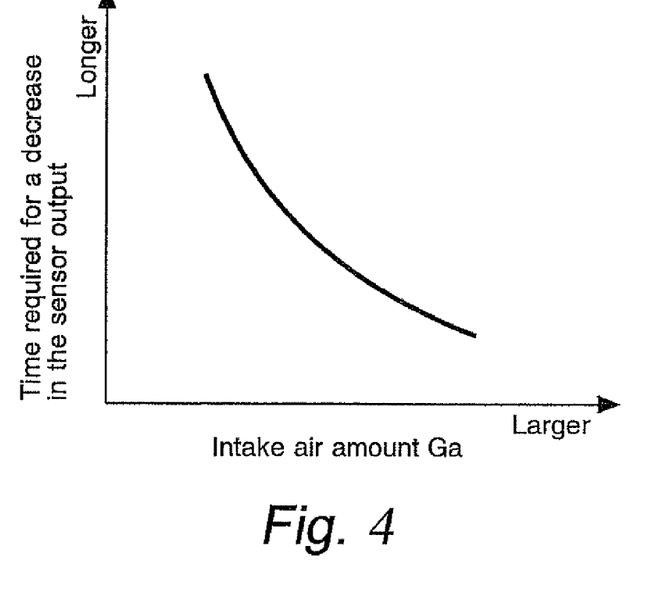
FIG. 4 is a diagram showing the time required for a decrease in the sensor output when a steady operation is performed at a certain intake air amount Ga after sensor element breakage.

(1) Conditions for Allowing the Exhaust Gas to Certainly Flow from a Defective Portion of the Sensor Element into the Atmospheric Layer FIG. 4 shows the time required for a decrease in the sensor output when a steady operation is performed at a certain intake air amount Ga after sensor element breakage. The "decrease in the sensor output" means that a subsequent fuel cut has decreased the sensor output value to the extent that a negative voltage is detected. As is obvious from FIG. 4, the larger the intake air amount Ga, the shorter the time required for a decrease in the sensor output. The larger the intake air amount Ga, the larger the amount of exhaust gas flowing in the exhaust path 14, and thus the higher the exhaust pressure. Therefore, the amount of exhaust gas flowing from a break in the sensor element to the atmospheric layer 54 increases with an increase in the intake air amount Ga.

Thus, the present embodiment makes the above-described abnormality diagnosis of the oxygen sensor when the time-integrated value SUM_Ga of the intake air amounts Ga is not smaller than an air amount that permits the exhaust gas to flow into the atmospheric layer 54. This makes it possible to avoid erroneously judging the sensor to be normal when it is abnormal due to its broken element, thereby enhancing the accuracy of detecting an abnormality caused by a broken element.

(2) Conditions for Preventing the Exhaust Gas from Flowing Back Toward the Exhaust Path after Flowing from a Break in the Sensor Element into the Atmospheric Layer As described above, when the integrated value SUM_Ga of the intake air amounts Ga is not smaller than a predetermined value, it can be concluded that the exhaust gas has certainly entered the atmospheric layer 54. However, if a small-Ga state, in which an intake air amount Ga remains small, subsequently persists for a long period of time, the exhaust gas may flow back toward the exhaust path 14 from the break in the sensor element.

Figure 5:
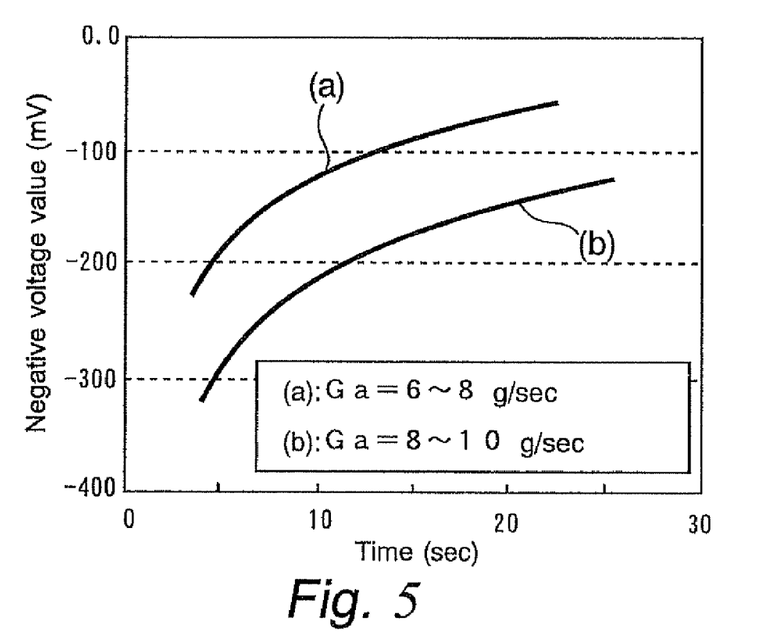
FIG. 5 is a diagram showing the relationship between a negative voltage value and the time during which a predetermined small-Ga value persists after the integrated value SUM_Ga of the intake air amounts Ga is equal to or greater than a predetermined value.

FIG. 5 shows the relationship between a negative voltage value and the time during which a predetermined small-Ga value persists after the integrated value SUM_Ga of the intake air amounts Ga is equal to or greater than a predetermined value. As indicated in FIG. 5, the absolute value of the negative voltage value tends to decrease with an increase in the length of the time during which the small-Ga value persists. Further, the absolute value of the negative voltage value tends to decrease with a decrease in the small-Ga value.

Consequently, if the small-Ga state, in which the exhaust gas that has flowed into the atmospheric layer 54 of the sensor flows back toward the exhaust path 14, continues for a predetermined period of time, the present embodiment prohibits the above-described abnormality diagnosis of the oxygen sensor. This makes it possible to avoid erroneously judging the sensor to be normal when it is abnormal due to its broken element, thereby enhancing the accuracy of detecting an abnormality caused by a broken element.

(3) Conditions for Generating a Negative Sensor Output Value Depending on the Status of the Exhaust Gas As described earlier, when a fuel cut is performed after the exhaust gas flows from a defective portion of the sensor element 44 into the atmospheric layer 54, the oxygen concentration difference between the atmospheric layer 54 side and exhaust path 14 side of the sensor element 44 is reversed, thereby resulting in the generation of a negative voltage. Therefore, when such a negative sensor output value is detected, it can be judged that the sensor element is broken.

Meanwhile, the exhaust gas flowing in the exhaust path 14 may become fuel-lean depending, for instance, on the operating status of the internal combustion engine. More specifically, a fuel-lean exhaust gas flows in the exhaust path 14 during, for instance, forced leanness control or fuel cut. In this instance, the lean gas has a high oxygen concentration. Therefore, even if a fuel cut is performed after the lean gas flows in from a break in the element, oxygen partial pressure difference is not likely to arise in the sensor element 44. This makes it difficult to accurately detect a sensor abnormality caused by its broken element.

As such being the case, the present embodiment prohibits the abnormality diagnosis of the oxygen sensor when the exhaust gas is fuel-lean. This makes it possible to avoid erroneously judging the sensor to be normal when it is abnormal due to its broken element, thereby enhancing the accuracy of detecting an abnormality caused by a broken element.

[Details of Process Performed by Present Embodiment]

Figure 6:
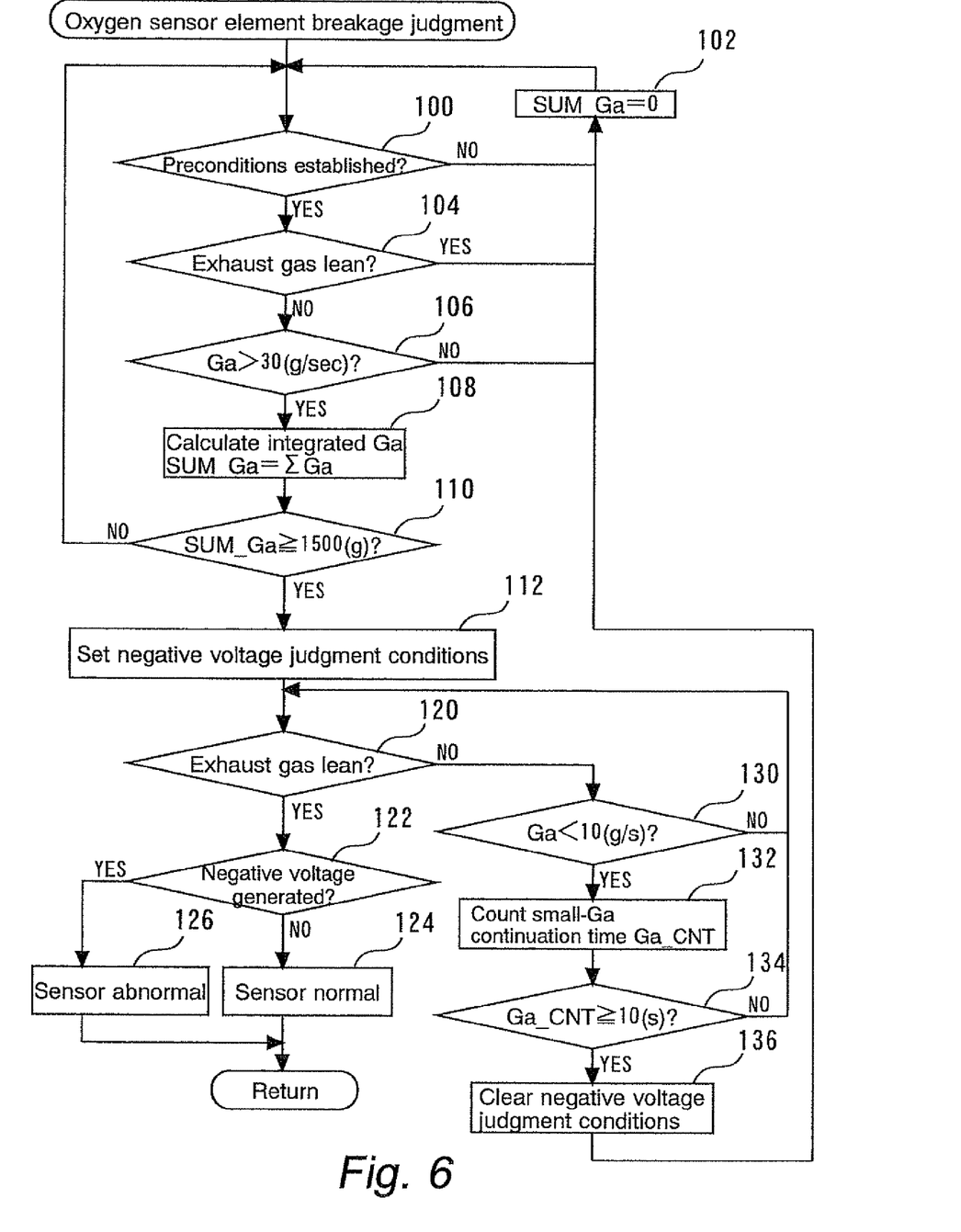
FIG. 6 is a flowchart for a routine executed by the system according to the first embodiment.

The process that the device according to the present embodiment performs to make a diagnosis of an abnormality caused by a broken element of the oxygen sensor 40 will now be described in detail with reference to FIG. 6. FIG. 6 is a flowchart illustrating a routine that the ECU 70 executes to make a diagnosis of an abnormality caused by a broken element of the oxygen sensor 40. First of all, the routine shown in FIG. 6 performs step 100 to judge whether preconditions are met. More specifically, step 100 is performed to judge whether the preconditions for making the abnormality diagnosis, such as the warm-up status of the internal combustion engine 10, vehicle velocity, engine speed NE, and activeness of the oxygen sensor 40, are satisfied. If the judgment result obtained in step 100 does not indicate that the preconditions are established, step 102 is performed so that an integrated Ga value, which is calculated in step 108 as described later, is reset to zero. The ECU 70 then starts the routine all over again.

If, on the other hand, the judgment result obtained in step 100 indicates that the preconditions are established, step 104 is performed to judge whether the exhaust gas is lean. As described earlier, while the exhaust gas is lean, a negative voltage may not be generated even after the lean gas flows in from a break in the sensor element. Such being the case, whether the exhaust gas is lean is determined in step 104 by judging whether a fuel cut is being performed in the internal combustion engine 10 or by judging whether forced leanness control is being exercised. If the judgment result obtained in step 104 indicates that the exhaust gas is lean, the routine proceeds to step 102 and resets the integrated Ga value. Subsequently, the ECU 70 starts the routine all over again.

If, on the other hand, the judgment result obtained in step 104 does not indicate that the exhaust gas is lean, step 106 is performed to judge whether the intake air amount Ga is greater than a predetermined value. Even when there is a break in the sensor element, the exhaust gas may not flow in from the break if the intake air amount Ga is extremely small. Therefore, step 106 is performed, more specifically, to judge whether the intake air amount Ga detected by the air flow meter 16 has reached a lower-limit value (e.g., Ga=30 g/s) for allowing the exhaust gas to flow in from a break in the element. If the judgment result obtained in step 106 does not indicate that the intake air amount Ga has reached the lower-limit value, the routine proceeds to step 102 and resets the integrated Ga value. Subsequently, the ECU 70 starts the routine all over again.

If, on the other hand, the judgment result obtained in step 106 indicates that the intake air amount Ga has reached the lower-limit value, step 108 is performed to calculate the integrated Ga value (SUM_Ga), which is the time-integrated value of the intake air amounts Ga. More specifically, step 108 is performed to calculate the time-integrated value of the intake air amounts Ga that is reached after a zero reset in step 102.

Next, step 110 is performed to judge whether the integrated Ga value (SUM_Ga) is not smaller than a predetermined value. As described earlier, the larger the intake air amount Ga, the larger the amount of exhaust gas that flows from a break in the sensor element to the atmospheric layer 54. Therefore, step 110 is performed, more specifically, to judge whether the integrated Ga value (SUM_Ga), which is calculated in step 106, has reached an air amount (e.g., SUM_Ga=1500 (g)) that causes the exhaust gas to certainly flow into the atmospheric layer 54. If the judgment result obtained in step 110 does not indicate that SUM_Ga≧1500, steps 100 to 108 are repeatedly performed for integration until the intake air amount Ga reaches the predetermined value.

If, on the other hand, the judgment result obtained in step 110 indicates that SUM_Ga≧1500, step 112 is performed to set negative voltage judgment conditions. The ECU 70 then concludes that the conditions where the exhaust gas in step 104 is not lean and the conditions where the SUM_Ga in step 110 is not smaller than the predetermined amount are established, and it proceeds to perform a later-described sensor output detection process.

Next, the routine shown in FIG. 6 performs step 120 to judge whether the exhaust gas is lean. As described earlier, when a lean gas flows toward the exhaust gas side of the sensor element 44 after the negative voltage judgment conditions are set in step 112, it is possible to judge whether the oxygen sensor 40 is normal or abnormal due to its broken element. More specifically, in step 120, whether the exhaust gas is lean is determined by judging whether a fuel cut is being performed in the internal combustion engine 10 or by judging whether forced leanness control is being exercised.

If the judgment result obtained in step 120 indicates that the exhaust gas is lean, the routine proceeds to step 122 and judges whether a negative voltage is output from the oxygen sensor 40. As described earlier, if the element of a sensor is broken when the exhaust gas is lean in a situation where the negative voltage judgment conditions are set, the oxygen partial pressure difference between the atmospheric layer side and exhaust gas side of the sensor element 44 is reversed. Therefore, whether the sensor is normal or abnormal can be accurately determined by judging whether a negative voltage is output from the sensor. As a result, the sensor is judged to be normal (step 124) when a negative voltage is not output from the oxygen sensor 40 and judged to be abnormal (step 126) when a negative voltage is output from the oxygen sensor 40.

If, on the other hand, the judgment result obtained in step 120 does not indicate that the exhaust gas is lean, the routine proceeds to step 130 and judges whether the intake air amount Ga is smaller than a predetermined amount. As described earlier, if the intake air amount Ga remains extremely small for a long period of time, the exhaust gas that has flowed into the atmospheric layer 54 may flow out from a break in the element. Therefore, step 130 is performed, more specifically, to let the air flow meter 16 detect the intake air amount Ga first and then judge whether the intake air amount Ga is smaller than a lower-limit value (e.g., Ga=10 g/s) that allows the exhaust gas, which has flowed into the atmospheric layer 54, to flow backward from the break. If the judgment result obtained in step 130 does not indicate that the intake air amount Ga is smaller than the lower-limit value, it is concluded that the exhaust gas does not flow outward as described above. Therefore, the routine returns to step 120 and judges the air-fuel ratio of the exhaust gas.

If, on the other hand, the judgment result obtained in step 130 indicates that the intake air amount Ga is smaller than the lower-limit value, the routine proceeds to step 132 to count small-Ga continuation time (Ga_CNT). As described earlier, when the intake air amount Ga becomes smaller than the lower-limit value for the small-Ga value, the exhaust gas in the atmospheric layer 54 may gradually flow out of a break in the element. Therefore, step 132 is performed to count the continuation time during which the exhaust gas may flow outward.

Next, step 134 is performed to judge whether the continuation time Ga_CNT counted in step 132 is not shorter than predetermined time. The predetermined time represents the time (e.g., 10 (s)) required for the exhaust gas to flow out of the atmospheric layer 54 to the extent that a subsequent abnormality diagnosis cannot be made. If the judgment result obtained in step 134 does not indicate that Ga_CNT≧10 (s), the routine concludes that an abnormality diagnosis of the oxygen sensor 40 can be made, returns to step 120, and judges the air-fuel ratio of the exhaust gas. If, on the other hand, the judgment result obtained in step 134 indicates that Ga_CNT≧10 (s), the routine concludes that an abnormality diagnosis of the oxygen sensor 40 cannot be made and performs step 136 to clear the negative voltage judgment conditions. Then, the routine resets the SUM_Ga to zero in step 102. Subsequently, the ECU 70 starts the routine all over again.

As described above, the device according to the present embodiment makes an abnormality diagnosis of the oxygen sensor 40 when the integrated value SUM_Ga of the intake air amounts Ga is not smaller than a predetermined value. Therefore, the abnormality diagnosis is made only when the exhaust gas can certainly enter the atmospheric layer from a break in the element. This makes it possible to avoid erroneously judging the sensor to be normal when it is abnormal due to its broken element, thereby enhancing the accuracy of detecting an abnormality caused by a broken element.

Further, when the intake air amount Ga remains not greater than a predetermined small-Ga value for a predetermined period of time, the present embodiment prohibits the aforementioned abnormality diagnosis of the oxygen sensor. Therefore, even when the element is broken, the abnormality diagnosis is prohibited in a situation where the exhaust gas in the atmospheric layer flows outward. This makes it possible to avoid erroneously judging the sensor to be normal when it is abnormal due to its broken element, thereby enhancing the accuracy of detecting an abnormality caused by a broken element.

Moreover, the present embodiment prohibits the abnormality diagnosis of the oxygen sensor when the exhaust gas is fuel-lean. Therefore, even when the exhaust gas certainly enters the atmospheric layer from a break in the element, the abnormality diagnosis is prohibited in a situation where no oxygen partial pressure difference arises between the exhaust gas side and atmospheric layer side. This makes it possible to avoid erroneously judging the sensor to be normal when it is abnormal due to its broken element, thereby enhancing the accuracy of detecting an abnormality caused by a broken element.

The embodiment described above makes a diagnosis of an abnormality caused by a broken element of the oxygen sensor 40 installed downstream of the catalyst 28. However, the target of abnormality diagnosis is not limited to the oxygen sensor 40. For example, the present invention may alternatively make the abnormality diagnosis of the air-fuel ratio sensor installed upstream of the catalyst.

Further, when a negative voltage is detected as the output of the oxygen sensor, the embodiment described above judges that the oxygen sensor is abnormal due to its broken element. However, the present invention is not limited to the use of such an abnormality judgment method. More specifically, if the occurrence of an abnormality is to be checked for in accordance with a change in the sensor output, a different output pattern may be used to formulate an abnormality judgment.

In the embodiment described above, the oxygen sensor 40 corresponds to the "exhaust gas sensor" according to the first aspect of the present invention. Further, the "judgment means" according to the first aspect of the present invention is implemented when the ECU 70 performs step 104; and the "abnormality diagnosis means" according to the first aspect of the present invention is implemented when the ECU 70 performs step 124 or 126.

Moreover, in the embodiment described above, the oxygen sensor 40 corresponds to the "exhaust gas sensor" according to the fourth aspect of the present invention. Further, the "integrated intake air amount acquisition means" according to the fourth aspect of the present invention is implemented when the ECU 70 performs step 108; the "judgment means" according to the fourth aspect of the present invention is implemented when the ECU 70 performs step 110; and the "abnormality diagnosis means" according to the fourth aspect of the present invention is implemented when the ECU 70 performs step 124 or 126.

Furthermore, in the embodiment described above, the oxygen sensor 40 corresponds to the "exhaust gas sensor" according to the seventh aspect of the present invention. In addition, the "cancellation means" according to the seventh aspect of the present invention is implemented when the ECU 70 performs step 136; and the "abnormality diagnosis means" according to the seventh aspect of the present invention is implemented when the ECU 70 performs step 124 or 126.

The invention claimed is:

1. An exhaust gas sensor abnormality diagnostic device comprising:
an exhaust gas sensor which is positioned in an exhaust path of an internal combustion engine, includes a sensor element positioned between external air and exhaust gas, and generates an output signal correlated with the oxygen partial pressure difference between the external air and the exhaust gas;
judgment means which judges whether execution conditions are established for making an abnormality diagnosis of element breakage in the exhaust gas sensor;
detection means which, when the execution conditions are judged to be established, detects an output signal generated by the exhaust gas sensor during a subsequent period during which an air-fuel ratio of exhaust gas is lean;
abnormality diagnosis means which, when the detected output signal is a negative voltage signal, judges that the exhaust gas sensor is abnormal due to a broken element thereof; and
cancellation means which cancels the establishment of the execution conditions when an intake air amount of the internal combustion engine remains not greater than a predetermined value for a predetermined period of time.

2. An exhaust gas sensor abnormality diagnostic device comprising:
an exhaust gas sensor which is positioned in an exhaust path of an internal combustion engine, includes a sensor element positioned between external air and exhaust gas, and generates an output signal correlated with the oxygen partial pressure difference between the external air and the exhaust gas;
a judgment device which judges whether execution conditions are established for making an abnormality diagnosis of element breakage in the exhaust gas sensor;
a detection device which, when the execution conditions are judged to be established, detects an output signal generated by the exhaust gas sensor during a subsequent period during which an air-fuel ratio of exhaust gas is lean;
an abnormality diagnosis device which, when the detected output signal is a negative voltage signal, judges that the exhaust gas sensor is abnormal due to a broken element thereof; and
a cancellation device which cancels the establishment of the execution conditions when an intake air amount of the internal combustion engine remains not greater than a predetermined value for a predetermined period of time.

* * * * *